United States Patent
Engel et al.

(10) Patent No.: US 9,512,559 B2
(45) Date of Patent: Dec. 6, 2016

(54) METHOD FOR CONFERRING ANTIMICROBIAL ACTIVITY TO A SUBSTRATE

(75) Inventors: Robert Engel, Carle Place, NY (US); Gary Innocenti, Mahwah, NJ (US); Karin Melkonian, Garden City, NY (US)

(73) Assignee: RESEARCH FOUNDATION OF THE CITY UNIVERSITY OF NEW YORK, New York, NY (US)

( * ) Notice: Subject to any disclaimer, the term of this patent is extended or adjusted under 35 U.S.C. 154(b) by 368 days.

(21) Appl. No.: 13/880,598

(22) PCT Filed: Aug. 26, 2011

(86) PCT No.: PCT/US2011/049373
§ 371 (c)(1),
(2), (4) Date: Sep. 26, 2013

(87) PCT Pub. No.: WO2012/054138
PCT Pub. Date: Apr. 26, 2012

(65) Prior Publication Data
US 2014/0294906 A1 Oct. 2, 2014

Related U.S. Application Data

(60) Provisional application No. 61/405,701, filed on Oct. 22, 2010.

(51) Int. Cl.
| | | |
|---|---|---|
| *A61L 2/18* | (2006.01) |
| *D06M 15/263* | (2006.01) |
| *C09D 5/14* | (2006.01) |
| *D06M 16/00* | (2006.01) |
| *D21H 21/36* | (2006.01) |
| *C08L 97/02* | (2006.01) |
| *D06M 13/325* | (2006.01) |
| *D06M 13/46* | (2006.01) |
| *B27K 3/15* | (2006.01) |
| *C08K 5/17* | (2006.01) |
| *C08L 31/04* | (2006.01) |
| *C08L 33/10* | (2006.01) |
| *D21H 13/26* | (2006.01) |
| *D21H 19/56* | (2006.01) |
| *D21H 21/34* | (2006.01) |
| *D21H 23/50* | (2006.01) |

(52) U.S. Cl.
CPC .............. *D06M 15/263* (2013.01); *A61L 2/18* (2013.01); *C08L 97/02* (2013.01); *C09D 5/14* (2013.01); *D06M 13/325* (2013.01); *D06M 13/46* (2013.01); *D06M 16/00* (2013.01); *D06M 16/003* (2013.01); *D21H 21/36* (2013.01); *B27K 3/153* (2013.01); *C08K 5/17* (2013.01); *C08L 31/04* (2013.01); *C08L 33/10* (2013.01); *D21H 13/26* (2013.01); *D21H 19/56* (2013.01); *D21H 21/34* (2013.01); *D21H 23/50* (2013.01); *Y10T 442/2525* (2015.04)

(58) Field of Classification Search
None
See application file for complete search history.

(56) References Cited

U.S. PATENT DOCUMENTS

| | | |
|---|---|---|
| 5,152,996 A | 10/1992 | Corey et al. |
| 7,491,753 B2 | 2/2009 | Krishnan |
| 2005/0132500 A1 | 6/2005 | Karl et al. |
| 2007/0166344 A1 | 7/2007 | Qu et al. |
| 2008/0145706 A1 | 6/2008 | Mevellec et al. |

FOREIGN PATENT DOCUMENTS

| | | | |
|---|---|---|---|
| EP | 1048422 A2 | 2/2000 | |
| EP | 1048422 A2 * | 11/2000 | ............... B27K 3/15 |
| JP | 2000073279 | 7/2000 | |
| WO | 2008128896 A2 | 10/2008 | |

* cited by examiner

*Primary Examiner* — Robert A Wax
*Assistant Examiner* — Melissa Mercier
(74) *Attorney, Agent, or Firm* — Hoffmann & Baron, LLP

(57) ABSTRACT

In one embodiment, the invention relates to a method for rendering a non-metallic substrate stably antimicrobial. The method comprises: (a) contacting the substrate with an antimicrobial surfactant; (b) contacting the substrate with a polymeric binder; and (c) subjecting the substrate, surfactant, and binder to conditions at which the substrate becomes stably antimicrobial. In another embodiment, the invention relates to a substrate into which an antimicrobial surfactant and a binder have penetrated.

29 Claims, No Drawings

METHOD FOR CONFERRING ANTIMICROBIAL ACTIVITY TO A SUBSTRATE

This application asserts the priority date of provisional patent application Ser. No. 61/405,701 filed on Oct. 22, 2010.

FIELD OF THE INVENTION

This invention relates to a novel process for rendering a substrate antimicrobial, and substrates made by the method.

BACKGROUND OF THE INVENTION

Current fears of antibiotic-resistant bacteria and other microbes as well as of bioterrorism have increased the importance of developing new ways to protect people from microbial infection. It is, for example, important to develop new materials for making clothing that can be more safely worn in contaminated environments. Such materials would be useful, for example, in hospitals and during military and civilian operations where bacterial contamination has occurred, or is expected.

In developing new antimicrobial compositions, it is important to discourage further antibiotic resistance. Ideally, therefore, novel antimicrobial compositions will function through non-specific, non-metabolic mechanisms.

For example, polycationic (quaternary ammonium) strings were developed in the laboratory of Robert Engel. See Fabian et al., Syn. Lett., 1007 (1997); Strekas et al., Arch. Biochem. and Biophys. 364, 129-131 (1999). These strings are reported to have antibacterial activity. See Cohen et al., Heteroat. Chem. 11, 546-555 (2000). Such strings may be attached to the surfaces of fabrics, rendering the surfaces antimicrobial. See, for example, U.S. Pat. No. 7,285,286.

It is also known to embed antimicrobial compounds in solid polymers. See U.S. patent application publication 2008/0300252.

Methods are also known that allow the coating of antimicrobial agents on surfaces. The coating may, however, wash or wear-off, causing the surface to be unprotected from microbes.

There is clearly a need for improved methods for making antimicrobial compositions and products. Ideally, the compositions and products do not lead to bacterial resistance, and the antimicrobial property is stable to multiple washes, especially to machine laundering.

In this invention, the inventors have developed new and more effective methods for surface modification to render surfaces antimicrobial with extended durability.

SUMMARY OF THE INVENTION

In one embodiment, the invention relates to a method for rendering a non-metallic substrate stably antimicrobial. The method comprises:
(a) contacting the substrate with an antimicrobial surfactant;
(b) contacting the substrate with a polymeric binder; and
(c) subjecting the substrate, surfactant, and binder to conditions at which the substrate becomes stably antimicrobial.

In another embodiment, the invention relates to a substrate into which an antimicrobial surfactant and a binder have penetrated.

In the method and the substrate described above, the binder is a homopolymer comprising monomers having the formula:

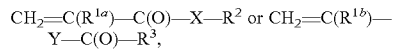

or a copolymer comprising monomers having the formula:

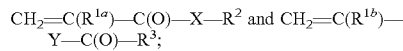

wherein:
X and Y independently represent O or $NR^4$;
$R^{1a}$ and $R^{1b}$ independently represent —H or —$CH_3$;
$R^2$ and $R^3$ independently represent an alkyl group having 1 to about 12 carbon atoms; and
$R^4$ represents —H, —$CH_3$, or —$CH_2CH_3$.

In yet another embodiment, the invention relates to a substrate rendered stably antimicrobial by the method.

DETAILED DESCRIPTION

Antimicrobial Activity

A substrate is antimicrobial if, following treatment according to the method of the invention, it inhibits growth of microbes, prevents the growth of microbes, or kills microbes. Preferably, the substrate is at least as antimicrobial as is shown for the samples processed in accordance with examples 1-3 below. More preferably, the substrate retains antimicrobial activity to a level of log 4-5 kill rate within 60 minutes of inoculation with, for example, approximately $5 \times 10^4$ S. aureus after the substrate is subjected to examples 1 and 2 below, and tested in accordance with example 3 below. Comparable results are obtained with MRSA and MSSA.

Microbes include, for example, bacteria and fungi, including yeast and mold. Some examples of bacteria include: S. aureus (methicilin resistant (MRSA) and methicilin sensitive (MSSA)), P. aeruginosa, S. faecalis, E. coli, K. pneumoniae, P. mirabilis, B. cepacia, MSSA, MRSA, E. faecalis, E. faecium, B. anthracis, B. subtilis, A. baumannii, and P. vulgaris. Some examples of fungi include: Candida SSP, Saccharomyces SSP, Aspergillus SSP, Stachybotrys SSP, Cladosporium SSP, Fusarium SSP, Penicillium SSP, and Mycotoxins SSP. Some examples of species of fungi include C. albicans, S. cerevisiae, A. fumigatus, A. flavus, A. niger, S. chartarum (atra) C. elatum, C. herbarum, C. sphaerospermum, C. cladosporioides, P. chrysogenum, P. citrinum, P. janthinellum, P. marneffei, and P. purpurogenum.

The Method

The method comprises:
(a) contacting the substrate with an antimicrobial surfactant;
(b) contacting the substrate with a polymeric binder; and
(c) subjecting the substrate, surfactant, and binder to conditions at which the substrate becomes stably antimicrobial.

Parts (a) and (b) of the method may be carried out separately in any order, or can be carried out simultaneously. For example, the process could be in the order (a), (b), (c); (b), (a), (c); or, alternatively, a mixture of the surfactant and the polymeric binder can be simultaneously contacted with the substrate.

The substrate is subjected to conditions at which: (i) the surfactant and the binder are stably incorporated into the substrate; and (ii) the substrate is not significantly degraded.

To be stably incorporated into the substrate in this specification means that the substrate can be subjected to multiple launderings and still retain antimicrobial activity at a level of a log 4-5 kill rate within about 60 minutes, preferably about 10 minutes, and more preferably about 2 minutes of being inoculated. A log 4-5 kill means that at least 99.99% to at least 99.999% of the bacteria are killed. The conditions the substrate is subjected to include, for example, heating, applying pressure, soaking in a suitable liquid, and combinations thereof.

The minimum temperature the substrate is subjected to is any temperature at which the surfactant and the binder are stably incorporated into the substrate. The minimum temperature may, for example, be about 70° F., preferably about 125° F., and more preferably about 200° F.

The maximum temperature is any temperature at which the substrate is not significantly degraded. Depending on the nature of the substrate, the maximum temperature may, for example, be about 600° F., preferably about 500° F., and more preferably about 400° F. A convenient temperature is about 250° F. to about 350° F., preferably about 275° F. to about 325° F., and more preferably about 300° F.

For example, polyesters degrade between about 482° F. and 550° F. Nylon 6.6 degrades at about 482° F. Nylon 6 degrades at about 416° F. Cotton, acrylics, and rayon should not be heated above about 340° F., and for not more than a few minutes at that temperature, e.g., not more than about 5 minutes, preferably not more than about 3 minutes, and more preferably not more than about 2 minutes.

The minimum pressure the substrate is subjected to is any pressure at which the surfactant is stably incorporated into the substrate. The minimum pressure may, for example, be about 1 bar, preferably about 3 bar.

The maximum pressure is any pressure at which the substrate is not significantly degraded. Depending on the nature of the substrate, the maximum pressure may, for example, be about 200 bar, preferably about 150 bar. For wood, the pressure should not exceed 16 bar, except that pressures up to 175 bar can be applied to wood without degradation if the pressure difference between the surface of the wood and the center does not exceed 16 bar. See Drescher et al., Wood and Wood Products 64, 178-182 (2006).

The substrate may also be soaked in a suitable liquid. The liquid may contain the surfactant and the binder. Alternatively, the substrate may be soaked in a suitable liquid before the substrate is contacted with the surfactant and binder. The liquid may be any liquid in which (i) the surfactant and the binder are stably incorporated into the substrate; and (ii) the substrate is not significantly degraded. Suitable liquids include, for example, water, methyl alcohol, ethyl alcohol, isopropyl alcohol, benzene, hexane, dimethyl sulfoxide, and tetrahydrofuran. The liquid may or may not comprise other chemical additives, such as, for example, acids, bases, or buffers.

The substrate is maintained under the conditions described above for a period of time sufficient to result in a log 4-5 kill of impinging microbes. This level of kill is to be accomplished within about 60 minutes of contact with the microbes, preferably within about 10 minutes, and more preferably within about 3 minutes in the instances of bacteria and fungi. In the instance of spores, this level of kill is to be accomplished within about 180 minutes, preferably about 120 minutes.

The amount of time the substrate is maintained under pressure or in a liquid as described above is preferably less than about 2 hours, preferably less than about 1 hour, and more preferably less than about 30 minutes. The amount of time the substrate is maintained at a temperature described above is preferably less than about 10 minutes, preferably less than about 5 minutes, and more preferably less than about 4 minutes.

The substrate may be contacted with the surfactant and the binder by methods known in the art. For example, the substrate, e.g., a fabric or wood, may be sprayed with liquid or a mist comprising a solution or suspension of the surfactant and binder. Spraying with the surfactant and the binder may be performed separately or simultaneously.

Alternatively, the fabric may successively be dipped in separate solutions or suspensions of the surfactant and binder, or be dipped in a solution or suspension comprising both surfactant and binder. In either case, the dipping is accomplished by methods well known in the art, for example, in a vat or by a continuous feed process. The surfactant and binder may also be wiped onto It is further contemplated that the surfactant and binder may be incorporated into a substrate by incorporating the surfactant and binder into a precursor of the substrate. For example, the surfactant and binder may be incorporated into a fiber, and then drawn into yarn and woven into a fabric. Alternatively, the surfactant and binder may be introduced into wood pulp and pressed into a board.

Substrate

The substrate may be any non-metallic filamentous, fibrous, or penetrable material. Some examples of suitable materials include wood, plastic, composites, paper. Such materials are useful in a variety of applications, such as, for example, building materials, toys, school supplies, office supplies, furniture and other home furnishings, etc.

In one embodiment, the substrate is a fabric or an article that comprises a fabric. Any kind of fabric is suitable for use with the method of the invention. The fabric may comprise natural polymers, synthetic polymers, or blends thereof. Some examples of fabrics include woven fabrics, knit fabrics, and engineered webs.

In this specification, a natural fiber comprises a naturally occurring polymer of a naturally occurring monomer, such as cellulose or amino acids. Some examples of natural fibers include cotton, wool, silk and latex and fur. Preferred natural fibers are cotton, wool, and silk. Other examples of natural fibers include cork and alginates.

A synthetic fiber comprises a manufactured polymer of a naturally or synthetically occurring monomer, such as a polyamide (e.g., nylon), a polyurethane (e.g., Spandex), a polyvinyl (e.g., polypropylene, polyvinyl chloride), a poly(meth)acrylate, a poly(meth)acrylamide, or a manufactured polycellulose (e.g., rayon).

In this specification, terms such as (meth)acrylate and (meth)acrylamide refer to acrylic and/or methacrylic carboxylates and carboxamides, respectively. The poly(meth)acrylate may be a polymer of (meth)acrylic acid or an ester of (meth)acrylic acid, such as a methyl or ethyl ester.

In another embodiment, the fabric comprises nylon. Nylon is a polymer that is made by condensing (a) a diamine having the formula $H_2N-(CH_2)_{n1}-NH_2$; and (b) a dicarboxylic acid having the formula $HO(O)C-(CH_2)_{n2}-C(O)OH$ or a derivative thereof having two activated carboxylate groups. Various types of nylon polymers and copolymers exist, depending, for example, on the length of the respective alkyl chains of the reactant alkyl diamines and alkyl carboxylates. Some examples of nylon polymers or copolymers include those wherein n1 represents 6 and n2 represents 6

(nylon 6,6), n1 represents 6 and n2 represents 12 (nylon 6,12), n1 represents 5 and n2 represents 10 (nylon 5,10), n1 represents 6 and n2 represents 11 (nylon 6,11), or n1 represents 10 and n2 represents 12 (nylon 10,12).

In a preferred embodiment, the substrate is a fire resistant or fire retardant fabric. The fabric may be rendered fire resistant or fire retardant by chemical treatment. Alternatively, fire resistant or fire retardant fibers may be made from polymers that are heat resistant.

In one embodiment, the heat resistant polymers for making fire resistant or fire retardant fabrics are aromatic polyamides, also known as aramids. The monomeric units of aramids may, for example, be —NH-AR—C(0)-, or —NH-AR—NH—C(O)-AR—C(0)- wherein AR represents an aromatic ring, usually phenylene. The groups on the phenylene moiety may be meta or para in orientation, i.e., meta-aramid or para-aramid, respectively. Commercial examples of meta-aramids and variations of meta-aramids include Nomex™ (DuPont), Teijinconex™ (Teijin, Holland, Japan), New Star™ (Yantai, China), X-Fiper™ (SRO Group, China), Kermel™ (Kermel, France). Commercial examples of para-aramids and variations of para-aramids include Kevlar™, (DuPont) and Twaron™ (Akzo/Teijin).

In one embodiment, the heat resistant polymers for making fire resistant or fire retardant fabrics are polybenzimidazoles, available from PBI Performance Products, Inc.

Surfactant

In general, the antimicrobial surfactant may be any anionic, cationic or non-ionic surfactant. The antimicrobial surfactants are capable of rendering a substrate stably antimicrobial when subjected to the method of the invention in accordance with the criteria described below.

Some examples of anionic surfactants include alkyl sulfates (e.g., ammonium lauryl sulfate, sodium lauryl sulfate; and sodium dodecyl sulfate); alkyl ether sulfates (e.g., sodium lauryl ether sulfate (SLES) and sodium myreth sulfate; sulfonates (e.g., docusates, dioctyl sodium sulfosuccinate, perfluorooctanesulfonate (PFOS), and perfluorobutanesulfonate); alkyl benzene sulfonates (e.g., ammonium lauryl benzene sulfonate, sodium lauryl benzene sulfonate; and sodium dodecyl benzene sulfonate); phosphates (e.g., alkyl aryl ether phosphate and alkyl ether phosphate); carboxylates (e.g., alkyl carboxylate salts, (e.g., soaps, such as sodium stearate, and sodium lauroyl sarcosinate).

Some examples of cationic surfactants include quaternary ammonium salts and phosphonium salts. The anion of the quaternary ammonium or phosphonium salts may be any anion, such as a halide (especially fluoride, chloride, and bromide), nitrate, sulfate, or phosphate. Some examples of quaternary ammonium salts include alkyltrimethylammonium chloride, cetyl trimethylammonium bromide (CTAB), cetyl trimethylammonium chloride (CTAC), cetylpyridinium chloride (CPC), benzalkonium chloride (BAC), benzethonium chloride (N-Benzyl-N,N-dimethyl-2-{2-[4-(2,4,4-trimethylpentan-2-yl)phenoxy]ethoxy}ethanaminium chloride, BZT), dimethyldioctadecylammonium chloride, dioctadecyldimethylammonium bromide (DODAB), 4-alkyl-1-aza-4-azoniabicyclo[2.2.2]octane, and 1,4-dialkyl-1,4-diazoniabicyclo[2.2.2]octane.

Some examples of non-ionic surfactants include Detsol-n (Intercon Co, St Louis, Mo.); triethanolamine; fatty alcohols, such as cetyl alcohol, stearyl alcohol, and oleyl alcohol; Polyoxyethylene glycol alkyl ethers (Brij) (e.g., $CH_3$—$(CH_2)_{10-16}$—$(O-C_2H_4)_{1-25}$—OH, such as octaethylene glycol monododecyl ether and pentaethylene glycol monododecyl ether; polyoxypropylene glycol alkyl ethers (e.g., $CH_3$—$(CH_2)_{10-16}$—$(O-C_3H_6)_{1-25}$—OH); Glucoside alkyl ethers (e.g., $CH_3$—$(CH_2)_{10-16}$—$(O\text{-Glucoside})_{1-3}$-OH, such as decyl glucoside, lauryl glucoside, octyl glucoside; Polyoxyethylene glycol octylphenol ethers: $C_8H_{17}$—$(C_6H_4)$—$(O-C_2H_4)_{1-25}$—OH, such as Triton X-100; polyoxyethylene glycol alkylphenol ethers; $C_9H_{19}$—$(C_6H_4)$—$(O-C_2H_4)_{1-25}$—OH, such as nonoxynol-9; glycerol alkyl esters, such as glyceryl laurate; polyoxyethylene glycol sorbitan alkyl esters (polysorbates); sorbitan alkyl esters (Spans); cocamide MEA, cocamide DEA, and dodecyldimethylamine oxide.

When an anionic surfactant, a cationic surfactant, or a non-ionic surfactant comprises an alkyl group, the preferred alkyl groups are chains having a minimum of about 8, preferably a minimum of about 10, and more preferably a minimum of about 12 carbon atoms in the chain. The maximum number of carbon atoms in the chain is about 24, preferably about 18, and more preferably about 16.

The Binder

The binder is a homopolymer comprising monomers having the formula $CH_2=C(R^{1a})-C(O)-X-R^2$ or $CH_2=C(R^{1b})-Y-C(O)-R^3$, or a copolymer comprising monomers having the formula $CH_2=C(R^{1a})-C(O)-X-R^2$ and $CH_2=C(R^{1b})-Y-C(O)-R^3$; wherein:

X and Y independently represent O or $NR^4$;

$R^{1a}$ and $R^{1b}$ independently represent —H or —$CH_3$;

$R^2$ and $R^3$ independently represent an alkyl group having 1 to about 12 carbon atoms; and $R^4$ represents —H, —$CH_3$, or —$CH_2CH_3$.

In a preferred embodiment, X and Y represent O; or $R^{1a}$ and $R^{1b}$ independently represent —H or —$CH_3$; $R^2$ and $R^3$ independently represent an alkyl group having 1 to about 12 carbon atoms; or $R^2$ and $R^3$ independently represent an alkyl group having 1 to 4 carbon atoms; or $R^4$ independently represents —H, —$CH_3$ or —$CH_2CH_3$.

In a more preferred embodiment, X and Y represent O; $R^{1a}$ and $R^{1b}$ independently represent —H or —$CH_3$; $R^2$ and $R^3$ independently represent an alkyl group having 1 to 4 carbon atoms; and $R^4$ independently represents —H, —$CH_3$ or —$CH_2CH_3$.

In a more preferred embodiment, the binder is a copolymer of butyl (meth)acrylate and vinyl acetate.

The polymer may be a homopolymer or a copolymer. The copolymer may be any known type of copolymer, e.g., a block copolymer, an alternating copolymer, a random copolymer, or combinations thereof. The polymer may have any molecular weight suitable for a fiber. A suitable minimum molecular weight is, for example, about 10,000 daltons, preferably about 40,000 daltons. A suitable maximum molecular weight is about 2,000,000 daltons, preferably about 700 daltons. The ratio of monomers in a copolymer may, for example, be about 20:1 to about 1:20.

Miscellaneous Definitions

In this specification, groups of various parameters containing multiple members are described. Within a group of parameters, each member may be combined with any one or more of the other members to make additional sub-groups. For example, if the members of a group are a, b, c, d, and e, additional sub-groups specifically contemplated include any two, three, or four of the members, e.g., a and c; a, d, and e; b, c, d, and e; etc.

In some cases, the members of a first group of parameters, e.g., a, b, c, d, and e, may be combined with the members of a second group of parameters, e.g., A, B, C, D, and E. Any member of the first group or of a sub-group thereof may be combined with any member of the second group or of a sub-group thereof to form additional groups, i.e., b with C; a and c with B, D, and E, etc.

With each group, it is specifically contemplated that any one or more members can be excluded. For example, if a group is said to contain a, b, c, d, and e, the group also may contain a, b, c, and e; a, b, and d; and a and d.

The compounds described in this specification are limited to those that are chemically feasible and stable. Therefore, a combination of substituents or variables in the compounds described above is permissible only if such a combination results in a stable or chemically feasible compound. A stable compound or chemically feasible compound is one in which the chemical structure is not substantially altered when kept at a temperature of 40° C. or less, in the absence of moisture or other chemically reactive conditions, for at least a week.

EXAMPLES

Example 1

Sample Preparation

Three samples of different types of fabrics were prepared, subjected to the method of the invention, and tested for antimicrobial activity. The three types of fabrics were 100% cotton, NYCO Marine Forest digital print, and silk (blue-commercial tie material).

The procedure for preparation of the samples for testing that resulted in resistance to decomposition through 50 washes was as follows. The samples to be treated were cut for each of the fabric samples into units of 30 cm×30 cm and weighed. Each was treated with separate solutions of agent and binder, being sprayed to full wetness with: a) a 10% aqueous solution of MB-80 (alkyldimethylbenzyl ammonium chloride, wherein the alkyl groups are straight chain having twelve (40%), fourteen (50%), and sixteen (10%) carbon atoms), and b) a 3% aqueous suspension of the binder, which is a copolymer emulsion of butyl acrylate and vinyl acetate. MB-80 is available from Lonza Inc (Allendale, N.J.). The binder is available from Celanese as emulsion product X-Link 2819 and Baker Adhesives (Paterson, N.J.) as resin emulsion 528).

The wet fabric, after dripping off excess liquid, was heated for 4 minutes at 143° C. After cooling, the fabric was again weighed, noting the increase in weight after addition of the antimicrobial agent and binder, and was ready for investigation.

Example 2

Procedure for Washing of Samples

Each of the types of modified cloth samples were divided into four equal sized pieces (30 cm×30 cm) that were stapled together such that testing samples could be removed from each in a known and specified manner. There were also included with these, similarly combined, samples of unmodified cloth of each particular type. In each instance the full stapled materials were subjected to the following washing and testing procedure.

For each type of modified cloth, the entire stapled set of samples was subjected to repeated washings according to the following procedure: the stapled were placed in an agitation system and vigorously agitated with 1.5 L water and 5 mL of detsol-n (Intercon, Co., St. Louis, Mo.) as the non-ionic detergent. After 30 minutes of such agitation at approximately 167° F., the complete set of fabric sample was removed from the wash system and thoroughly rinsed with 3 L of water in 6 washings, and residual water removed prior to air-drying by suction. The complete set of fabric samples was then air-dried. From the individual pieces of both treated and unmodified cloth were cut 1 cm×30 cm samples for testing. The remainder of each set of samples was returned for continued successive washing studies. Samples were taken after specified numbers of washings for testing, through 50 washes according to this procedure.

Example 3

Testing of Washed Samples

Samples were tested by the addition of approximately $5 \times 10^4$ bacteria (*S. aureus*) directly on a piece of either treated or untreated cloth (1.5 cm×1.5 cm) for two minutes. Samples were then placed in 4 mL of growth media (bacto-tryptone, bacto-agar, yeast extract, sodium chloride) and incubated at 37° C. overnight in a shaking water bath. Samples were examined visually for turbidity caused by the growth of the bacteria. All samples were tested in duplicate.

| | Material | Results |
|---|---|---|
| 1 | 100% cotton | Log 4-5 kill after 50 washings |
| 2 | NYCO Marine Forest digital print | Log 4-5 kill after 50 washings |
| 3 | silk (blue commercial tie material) | Log 4-5 kill after 50 washings |

Turbidity was used as a measure of the number of bacteria present. The turbidity of the treated growth medium associated with the treated fabric was compared to that of the growth medium associated with incubated samples of untreated fabric. For determination of log 4-5 kill, the incubated fabrics, both treated and untreated, were plated for comparison, and the number of colonies generated were hand counted under a microscope. Similar results were obtained for samples fabric containing 95% polyester/5% lycra.

What we claim is:

1. A method for rendering a non-metallic substrate stably antimicrobial, the method comprising:
    (a) contacting the substrate with an antimicrobial surfactant;
    (b) contacting the substrate with a polymeric binder; and
    (c) subjecting the substrate, surfactant, and binder to conditions at which the substrate becomes stably antimicrobial;
    wherein the binder is a homopolymer comprising monomers having the formula $CH_2=C(R^{1a})-C(0)-X-R^2$ or $CH_2=C(R^{1b})-Y-C(0)-R^3$, or a copolymer comprising monomers having the formula $CH_2=C(R^{1a})-C(0)-X-R^2$ and $CH_2=C(R^{1b})-Y-C(0)-R^3$;
    wherein:
    X and Y independently represent 0 or $NR^4$;
    $R^{1a}$ and $R^{1b}$ independently represent —H or —$CH_3$;
    $R^2$ and $R^3$ independently represent an alkyl group having 1 to about 12 carbon atoms; and
    $R^4$ represents —H, —$CH_3$, or —$CH_2CH_3$;

wherein the substrate is contacted first with the antimicrobial surfactant and then with the binder.

2. The method of claim 1, wherein the act of rendering a substrate antimicrobial inhibits the growth of bacteria, mold, and fungus.

3. The method of claim 1, wherein the substrate, surfactant, and binder are maintained at a minimum temperature of about 70° F. and a maximum temperature of about 600° F., or any temperature therebetween.

4. The method of claim 1, wherein the antimicrobial surfactant and the binder are sprayed onto the substrate.

5. The method of claim 1, wherein substrate is dipped into a solution or a suspension comprising the antimicrobial surfactant and the binder.

6. The method of claim 1, wherein the substrate is filamentous, fibrous, or penetrable.

7. The method of claim 1, wherein the substrate is filamentous or fibrous.

8. The method of claim 1, wherein the substrate is selected from the group consisting of wood, plastic, composites, and paper.

9. The method of claim 1, wherein the substrate is a fabric.

10. The method of claim 9, wherein the substrate is heat resistant fabric.

11. The method of claim 9, wherein the fabric comprises a natural polymer, a synthetic polymer, or a blend thereof.

12. The method of claim 11, wherein the fabric comprises a natural polymer.

13. The method of claim 12, wherein the natural polymer is selected from the group consisting of cotton, wool, silk, latex, fur and blends thereof.

14. The method of claim 11, wherein the fabric comprises a synthetic polymer selected from the group consisting of synthetic polymer a polyamide, a polyurethane, a polyvinyl, a poly(meth)acrylate, a poly(meth)acrylamide, a polycellulose, and blends thereof.

15. The method of claim 14, wherein the synthetic polymer is nylon, spandex, polypropylene, rayon, and blends thereof.

16. The method of claim 1, wherein the antimicrobial surfactant is an anionic, cationic, or non-ionic surfactant.

17. The method of claim 16, wherein the antimicrobial surfactant is a non-ionic antimicrobial surfactant selected from the group consisting of detsol-n, triethanolamine, and Triton X-100.

18. The method of claim 16, wherein the antimicrobial surfactant is an anionic surfactant selected from the group consisting of alkyl carboxylates, alkyl sulfates, alkyl sulfonates, and alkyl benzene sulfonates.

19. The method of claim 1, wherein the antimicrobial surfactant is a quaternary ammonium salt.

20. The method of claim 1, wherein X and Y represent O.

21. The method of claim 1, wherein R1a and R1b independently represent —H or —CH3.

22. The method of claim 1, wherein R2 and R3 independently represent an alkyl group having 1 to about 12 carbon atoms.

23. The method of claim 1, wherein R2 and R3 independently represent an alkyl group having 1 to 4 carbon atoms.

24. The method of claim 1, wherein R4 independently represents —H, —CH3 or —CH2CH3.

25. The method of claim 1, wherein the binder is a copolymer of butyl (meth)acrylate and vinyl acetate.

26. The method of claim 1, wherein the binder comprises a copolymer having a ratio of monomers of CH2=C(R1a)-C(O)—X—R2 and monomers of CH2=C(R1b)—Y—C(O)—R3 is 20:1 to 1:20.

27. The method of claim 1, wherein the binder comprises a block copolymer.

28. The method of claim 1, wherein the binder comprises a polymer or copolymer having a minimum molecular weight of about 10,000 daltons and a maximum molecular weight of about 2,000,000 daltons.

29. A method for rendering a non-metallic fabric stably antimicrobial, the method comprising:
(a) contacting the fabric with an antimicrobial surfactant;
(b) contacting the fabric with a polymeric binder; and
(c) subjecting the fabric, surfactant, and binder to conditions at which the fabric becomes stably antimicrobial;
wherein the binder is a homopolymer comprising monomers having the formula $CH_2=C(R^{1a})—C(0)\text{-}X—R^2$ or $CH_2=C(R^{1b})—Y—C(0)\text{-}R^3$, or a copolymer comprising monomers having the formula $CH_2=C(R^{1a})—C(0)\text{-}X—R^2$ and $CH_2=C(R^{1b})—Y—C(0)\text{-}R^3$;
wherein:
X and Y independently represent 0 or $NR^4$;
$R^{1a}$ and $R^{1b}$ independently represent —H or —$CH_3$;
$R^2$ and $R^3$ independently represent an alkyl group having 1 to about 12 carbon atoms; and
$R^4$ represents —H, —$CH_3$, or —$CH_2CH_3$.

* * * * *